United States Patent [19]

Glander et al.

[11] 4,368,421

[45] Jan. 11, 1983

[54] FREQUENCY MODULATED MICROWAVE IN COMBINATION WITH A VOLTAGE DETECTOR AND COMPARATOR DEVICE FOR MEASURING A VARYING MOISTURE CONTENT OF SHEET-LIKE SAMPLES

[75] Inventors: Siegfried Glander, Bad Soden am Taunus; Franz Lappe, Hofheim am Taunus, both of Fed. Rep. of Germany

[73] Assignee: Hoechst Aktiengesellschaft, Frankfurt am Main, Fed. Rep. of Germany

[21] Appl. No.: 175,779

[22] Filed: Aug. 6, 1980

Related U.S. Application Data

[63] Continuation of Ser. No. 858,893, Dec. 8, 1977, abandoned.

[30] Foreign Application Priority Data

Dec. 10, 1976 [DE] Fed. Rep. of Germany ... 7638683[U]

[51] Int. Cl.³ .................... G01R 27/04; G01N 22/04
[52] U.S. Cl. ............................................. 324/58.5 A
[58] Field of Search ..................... 324/58 A, 58.5 A

[56] References Cited

U.S. PATENT DOCUMENTS

| | | | |
|---|---|---|---|
| 3,060,421 | 10/1962 | Rideout | 324/58.5 A UX |
| 3,155,898 | 11/1964 | Chope | 324/58.5 A |
| 3,498,112 | 3/1970 | Howard | 324/58.5 A |
| 3,501,692 | 3/1970 | Kluck | 324/58.5 A |
| 3,534,260 | 10/1970 | Walker | 324/58.5 A |
| 3,551,806 | 12/1970 | Sasaki | 324/58.5 A |
| 3,599,089 | 8/1971 | Bugnolo | 324/58.5 A |
| 3,810,005 | 5/1974 | Bennion et al. | 324/58.5 A |
| 3,913,012 | 10/1975 | Kujath | 324/58.5 A |

FOREIGN PATENT DOCUMENTS 226899 1/1969 U.S.S.R. .................... 324/58.5 A

*Primary Examiner*—Gerard R. Strecker
*Attorney, Agent, or Firm*—Curtis, Morris & Safford

[57] ABSTRACT

The device for measuring the moisture content of a sheet-like sample consists of a microwave oscillator, microwave transmitter and microwave receiver. At least three horn transmitters are flanged via an attenuator, directional couplers and attenuators to a frequency modulated microwave oscillator, opposite each of the horn transmitters, which are fixed on a frame, a microwave receiver with detector is arranged on the same frame, and a reference detector is flanged, via an attenuator, to at least one of the directional couples. The microwave receivers can be arranged so that they can be moved on the frame.

7 Claims, 1 Drawing Figure

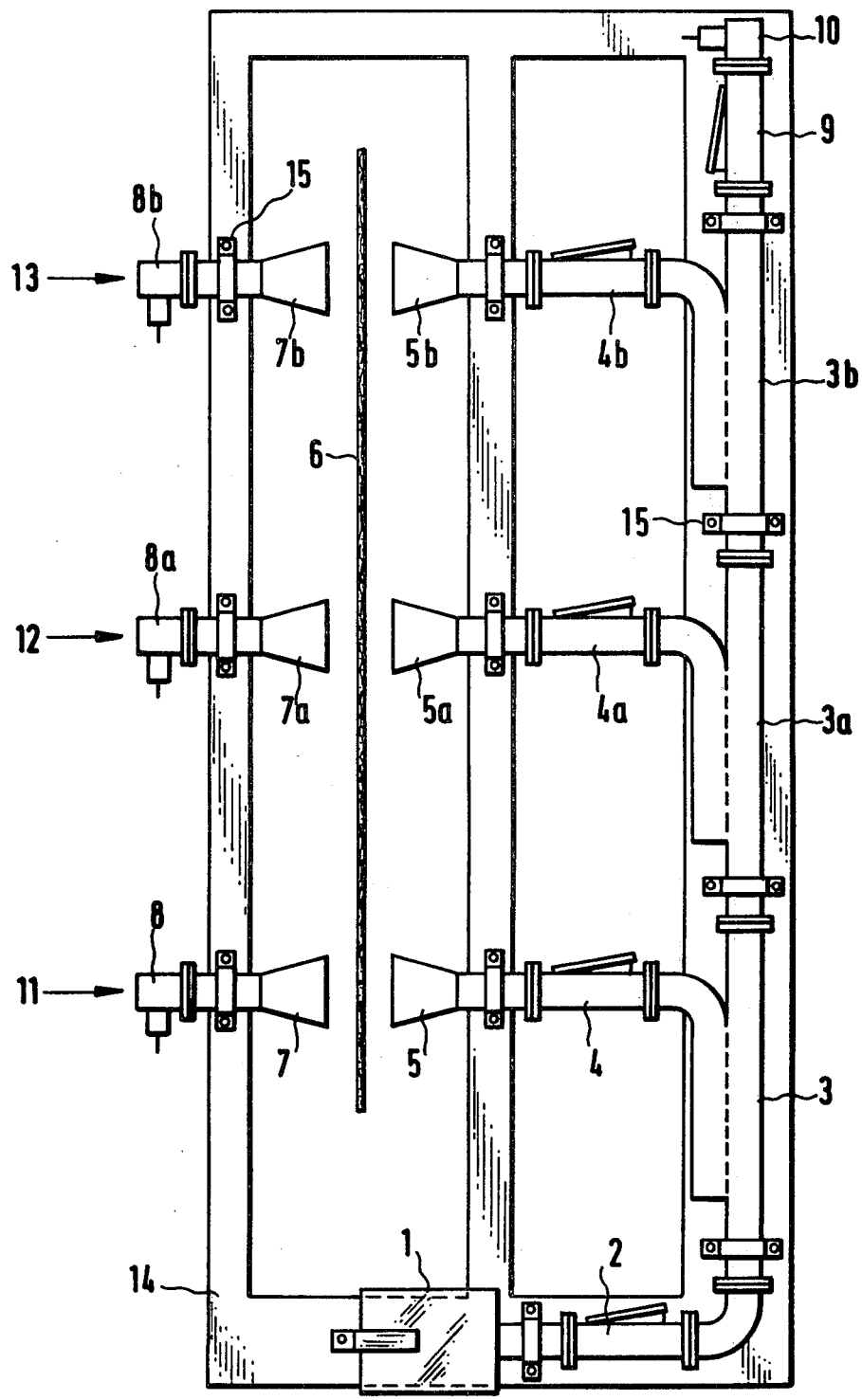

FREQUENCY MODULATED MICROWAVE IN COMBINATION WITH A VOLTAGE DETECTOR AND COMPARATOR DEVICE FOR MEASURING A VARYING MOISTURE CONTENT OF SHEET-LIKE SAMPLES

This is a continuation of application Ser. No. 858,893, filed Dec. 8, 1977, now abandoned.

The subject of the invention is a device for simultaneously measuring the moisture content at the sides and in the centre of sheet-like samples or of sample webs (textile webs, paper webs, plastic webs, rubber webs, plastic and wood panels, and the like) with microwaves.

In the continuous dyeing and finishing of textile webs a uniform application of liquor is required. For this reason the padding mangle is still, at present, the most widely used machine for applying liquor. The pick-up of the padding mangle can be altered across the width of the textile webs, depending on the design, by pressure on the journals of the slightly convexly ground rolls or, in the case of floating rolls, by pressure on the journals and additional pressure on the fluid in which the one or both rolls float. There are also designs of padding mangles in which pressure can be applied separately on the journals and in the centre of the pair of rolls. With all types of padding mangles it is desirable, and also adequate, to measure the amount of applied moisture at the sides and in the centre of the material web, for monitoring and controlling a uniform application of liquor across the whole width of the material. Microwave moisture-measuring instruments are suitable for determining the amount of applied liquor in the high moisture range. The equipment consists of a microwave oscillator, a microwave transmitter and a microwave receiver. The disadvantage with the known equipments is that with them only the moisture at one particular part, for example at the centre, at the edge, and the like, of the textile web can be sampled at a time. From such a measurement no conclusions can, however, be drawn as to the moisture distribution across the whole width of the web. Traversing microwave instruments which operate by reflection have failed in practice and are therefore not used. The adjustment of the equipment was too difficult and the fluttering of the wet material web caused errors in the measurement results.

The object was therefore to provide a device with which the moisture application can be measured simultaneously at the sides and in the centre of sheet-like samples, in particular sample webs, and with which the fluttering of the wet sample web no longer has an effect.

For achieving the object a device has now been found for measuring the moisture content of a sheet-like sample with microwaves, which device consists of a microwave oscillator, microwave transmitter and microwave receiver wherein at least three horn transmitter are flanged via an attenuator, directional couplers and attenuators to a frequency modulated microwave oscillator, opposite each of the horn transmitters, which are fixed on a frame, a microwave receiver with detector is arranged on the same frame, and a reference detector is flanged, via an attenuator, to at least one of the directional couplers.

The microwave receivers can be arranged so that they can be moved on the frame.

Moisture contents from about 30 g of water to about 600 g of water per m² can be determined with the device. It is thus possible for differences of water content of 1–3% from measuring position to measuring position to be measured reproducibly.

If with other application equipment such as, for example, spraying and foam equipment, or behind pre-drying units such as infra-red pre-driers, three measuring positions across the web width are not adequate for monitoring the uniform moisture content, further measuring positions can be flanged on, via additional directional couplers, in addition to the three described.

In the following text the device is described in an illustrative embodiment.

The FIGURE shows a schematic representation of the device for measuring the moisture content on the sides and in the center of webs, such as for example textile webs, paper webs, and the like.

The microwaves of about 2.4 to 3.7 cm wavelength, produced in the frequency modulated microwave oscillator 1, pass, via the attenuator 2, into the directional couplers 3, 3a, 3b which have a coupling factor of, for example, 3 dB. These three directional couplers couple in each case a part of the microwave power into the three measuring paths 11, 12 and 13, which consist of the attenuators 4, 4a, 4b, the horn transmitters 5, 5a, 5b, the receivers 7, 7a, 7b and the detectors 8, 8a, 8b. The sample web 6 runs between the transmitters and receivers. Microwave power is absorbed on penetrating the sample and specifically as a function of the moisture content of the sample. The part of the microwave power which is not coupled out by the three directional couplers 3, 3a, 3b passes through the attenuator 9 into the detector 10. The whole device is arranged on a frame 14 by means of fasteners 15. In the case of wider sample webs, straight waveguides can also be flanged on between the directional couplers 3, 3a, 3b.

The voltage resulting at the detector 10 can be calibrated to indicate the absolute amount of water in grams of water per m². The voltages at the detectors 8, 8a, 8b serve to show the difference in the moisture content at the edges and in the centre of the sample web. For this purpose the attenuators 4, 4a, 4b, are set without the sample web, in such a way that the same microwave powers are indicated in the measuring paths 11, 12 and 13 by the detectors 8, 8a, 8b. The voltage value indicated by one detector, for example 8a, behind the material web, is held to the preset voltage value by reduction of the attenuation in the attenuator 2, even when a wet sample web absorbs a part of the microwave power. The attenuation of the microwave power is altered as a function of the moisture content in such a manner that the detector voltage, for example at 8a, is always constant. As a result, at a higher moisture content a higher voltage results at the detector 10. Differing voltage values at the detectors 8 and 8b, compared with 8a, signify differing moisture across the width of the material web. The attenuation of the microwaves at the position 2 can be effected by hand or regulated automatically with an attenuator which can be controlled electronically, for example with the Model 704 from Messrs. Rohde & Schwarz, D-8000 Munich. If diodes with square-law characteristic curves are chosen for the detectors the resulting direct current voltage is proportional to the particular microwave power passing into the detectors.

The outputs of the detectors 8, 8a, 8b and 10 are connected to an indicating instrument, for example a pen recorder—which is not represented. The output voltages are suitable in particular for controlling a uniform application of liquor across the width of the material web and also for controlling a uniform drying across the width of the material web.

What is claimed is:

1. A device for measuring the moisture content of a sheet-like sample with microwaves, which device comprises:
   a microwave oscillator for providing an output of microwaves;
   at least three horn transmitters;
   a microwave receiver positioned opposite each horn transmitter, said horn transmitters and receivers being positioned so that a different portion of said sheet-like sample can pass between each of said transmitters and its associated receiver;
   a separate microwave detector for producing an output signal having a signal level value which has a correspondence to the detected signal level value of microwaves received by each of said receivers at a set point condition;
   a microwave distributing means for distributing a portion of the microwave output of said oscillator to each of said horn transmitters, said distributing means including directional couplers and also including a separately adjustable attenuator for each said horn transmitter such that the ratios between the signal level values of the output signal values produced by each of said detectors can be set to desired signal values at said set point conditions when the relative amount of moisture of said sheet-like sample placed between the horn transmitters and receivers associated with said detectors is known for each location between each of said transmitters and receivers;
   means for controllably attenuating the level of the microwave output of said oscillator which attenuating microwave output is supplied to said distributing means such that the signal level output of one of said detectors tends to remain constant and interrelated to said means for controllably attenuating said oscillator, and
   means including said separate microwave detector for measuring the relative signal level value of the microwave output which is supplied to said distributing means and detected at the other remaining detectors for measuring the moisture of the sheet-like sample and comparing, with the signal level output of each of the other remaining detectors, said signal value detected by said separate detector.

2. A device for measuring the moisture content of a sheet-like sample with microwaves, which device comprises:
   a microwave oscillator for providing an output of frquency modulated microwaves;
   at least three horn transmitters;
   a separate microwave receiver positioned opposite each horn transmitter, said horn transmitters and receivers being positioned so that a different portion of said sheet-like sample can pass between each said transmitter and its associated receiver;
   a microwave detector for each of said receivers for simultaneously producing an output signal having a signal level value which corresponds to the signal level value of microwaves received by each of said receivers;
   a microwave distributing means for simultaneously distributing a portion of the microwave output of said oscillator to each of said horn transmitters, said distributing means including directional couplers and also including a separately adjustable attenuator for each of said horn transmitters such that the ratios between the signal level values of the output signals produced by each of said detectors can be set to a set point value at a time when the relative amount of moisture placed between the horn transmitters and receivers associated with said detectors is known and is uniform;
   means for controllably attenuating the energy value of the microwave output of said oscillator supplied to said distributing means such that the detected signal value output of one of said detectors tends to remain constant, said detector being interrelated, based on said constant signal value, to said means for controllably attenuating said microwave energy value, and
   means including an additional microwave detector for measuring the relative signal level value of the microwave output which is supplied to said distributing means and detected at each of the other microwave detectors for measuring the moisture of the sheet-like sample and comparing with the signal level output of each of the other remaining detectors said signal value detected by said separate detector.

3. A method for measuring the moisture content of a sheet-like sample with microwaves, which method comprises the steps of:
   generating an output of microwaves;
   distributing said output of microwaves to at least three moisture sensing channels;
   generating a separate output signal for each of said channels, the signal level value of which corresponds to the signal level value of microwaves passing through one of said channels;
   attenuating said output of microwaves which is distributed to said channels in response to successive changes in one of said output signals so as to tend to keep the level of said one output signal constant;
   detecting the changing level of said attenuated output of microwaves at the output of each of the channels, and
   continually adjusting the attenuation of said output of microwaves relative to one output with constant signal value to keep that signal value at a set point and comparing that value with detected signal values of the other output values detected at the other channels to provide a measurement of moisture content of the sheet-like sample.

4. A method according to claim 3, wherein said output of microwaves is distributed to said channels simultaneously and wherein the generation of said separate output signals for each channel and the detecting of the signal level of said attenuated output of microwaves are performed simultaneously.

5. A method according to claim 3, wherein said generating of an output of microwaves includes the generation of frequency modulated microwaves.

6. A method for measuring the moisture content of a sheet-like sample with microwaves, which method comprises the steps of:
   generating an output of microwaves;
   distributing said output of microwaves to at least three moisture sensing channels;
   generating a separate output signal for each of said channels, the level of which corresponds to the level of microwaves passing through one of said channels;

adjustably attenuating the relative level of microwaves supplied to each of said channels at a time when the relative amount of moisture in said channels is known, said adjustable attenuation being performed until the ratios between the levels of said output signals have desired values, and when a sample whose moisture content is to be measured is passed through said channels, attenuating said output of microwaves which is distributed to said channels in response to one of said output signals so as to tend to keep the level of said one output signal constant, and detecting the level of said attenuated output of microwaves.

7. A method according to claim 6, wherein said step of adjustably attenuating the relative level of microwaves supplied to each of said channels is conducted when no sample is placed in said channels, and said adjustable attenuation continues until the levels of all the output signals are equal.

* * * * *